United States Patent [19]
Plazenet et al.

[11] Patent Number: 6,020,589
[45] Date of Patent: Feb. 1, 2000

[54] NUCLEAR MEDICINE MACHINE

[75] Inventors: Jean Plazenet, St Hilaire, France; Philippe Van Boxem, Waterloo, Belgium

[73] Assignee: SMV International, Buc, France

[21] Appl. No.: 08/924,433

[22] Filed: Aug. 27, 1997

[30] Foreign Application Priority Data

Aug. 30, 1996 [FR] France .................................. 96 10650

[51] Int. Cl.[7] .................................................. G01T 1/166
[52] U.S. Cl. .............................. 250/363.04; 250/363.05; 250/363.08
[58] Field of Search ........................ 250/363.04, 363.05, 250/363.03, 363.08

[56] References Cited

U.S. PATENT DOCUMENTS

| | | | |
|---|---|---|---|
| 4,095,107 | 6/1978 | Genna et al. | 250/363.04 |
| 5,591,977 | 1/1997 | Green et al. | 250/363.04 |
| 5,691,538 | 11/1997 | Ohike et al. | 250/363.04 |
| 5,798,527 | 8/1998 | Muehllehner et al. | 250/363.03 |

FOREIGN PATENT DOCUMENTS 2697918  5/1994  France .

*Primary Examiner*—Constantine Hannaher
*Attorney, Agent, or Firm*—Nilles & Nilles SC

[57] ABSTRACT

To reduce the costs of manufacture of a nuclear medicine machine, there is provided a machine whose detector is not mobile. In order, nevertheless, to give it extensive possibilities of adaptation, an input face of the detector is made in a concave curved shape. As a variant, with a mobility that is simple to achieve, it is even possible to take account of the differences in size among patients.

17 Claims, 3 Drawing Sheets

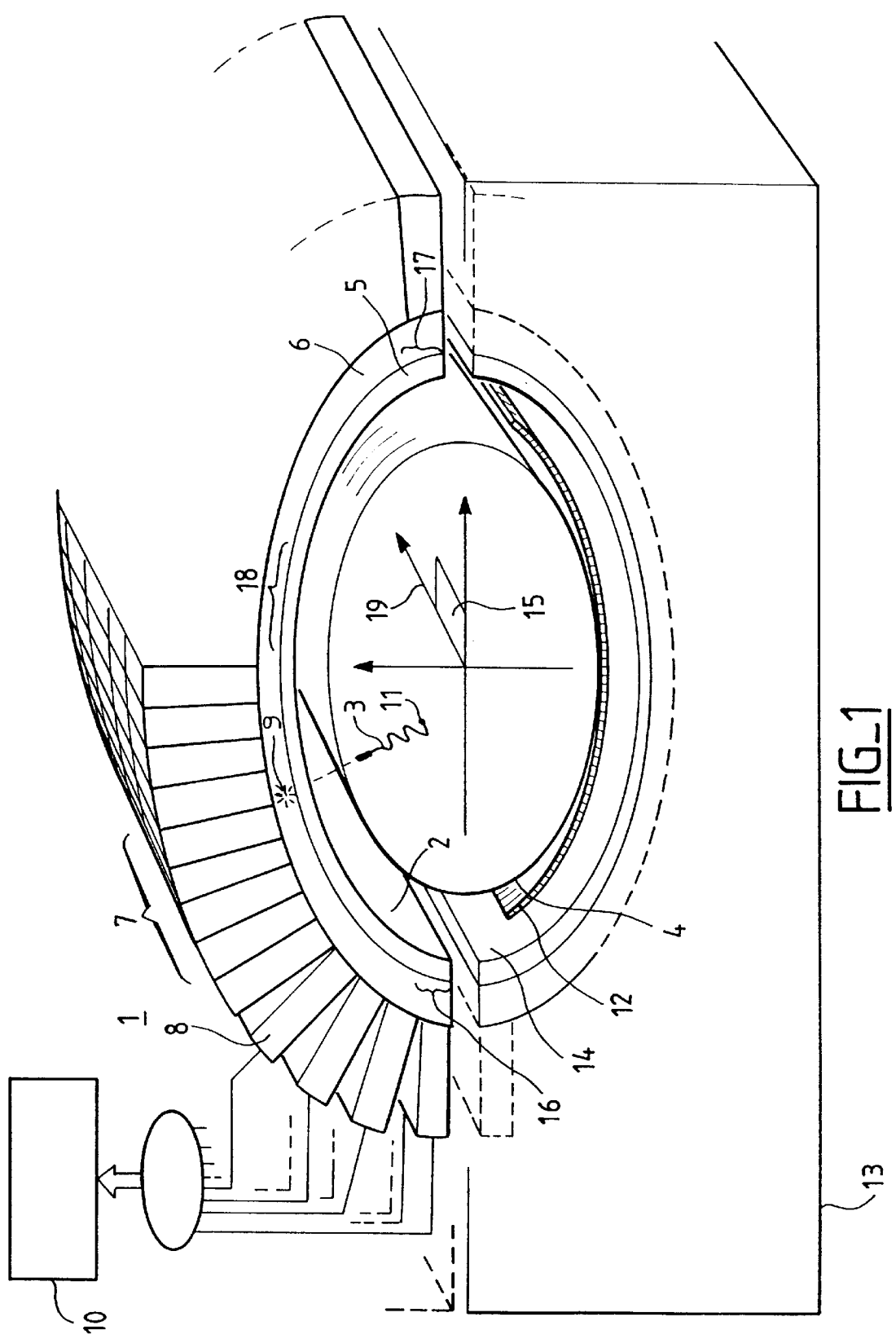
FIG_1

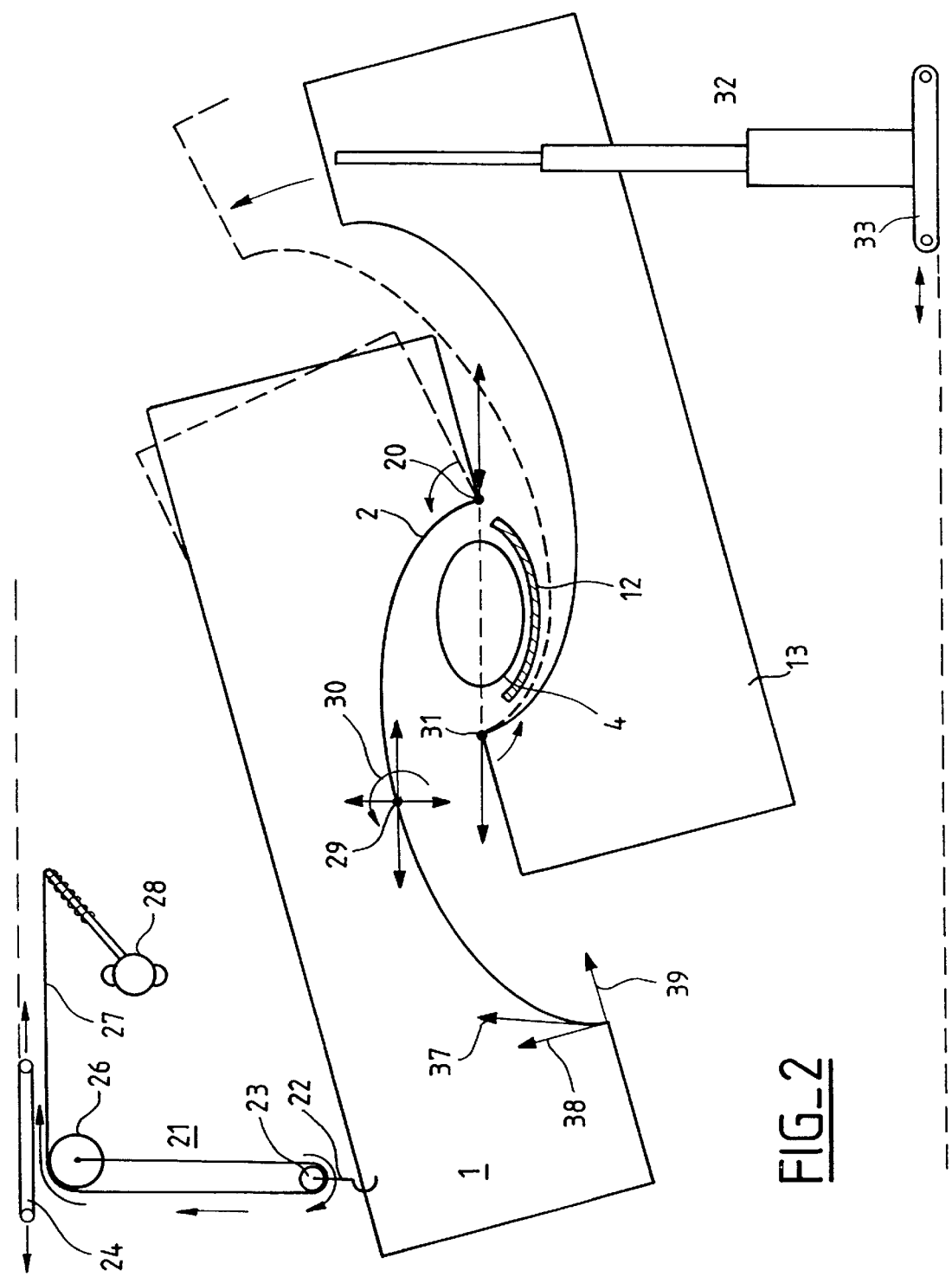
FIG_2

FIG_3
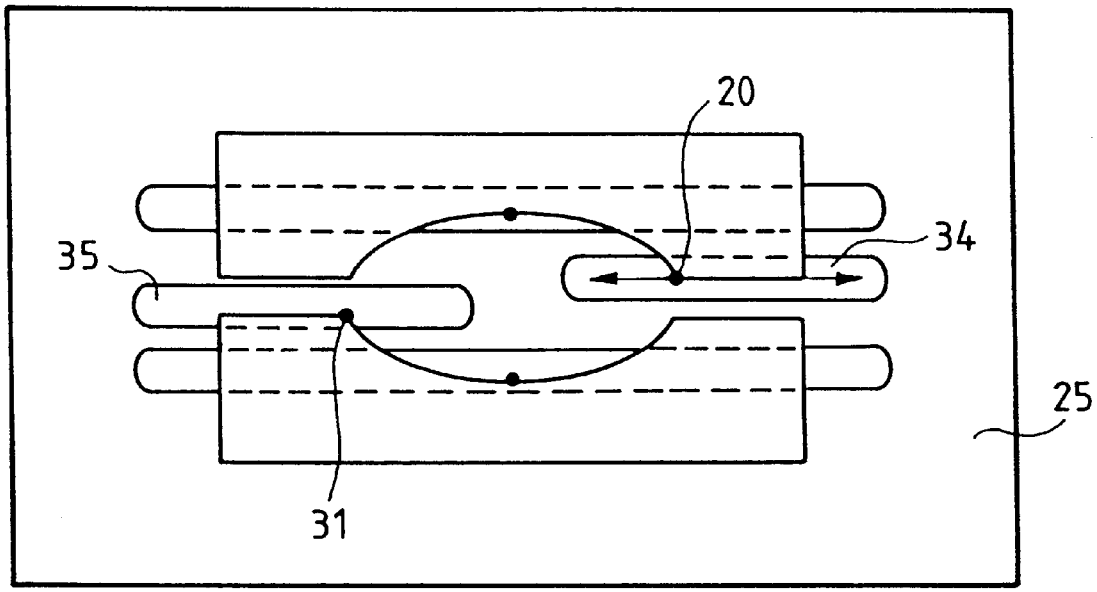
FIG_4
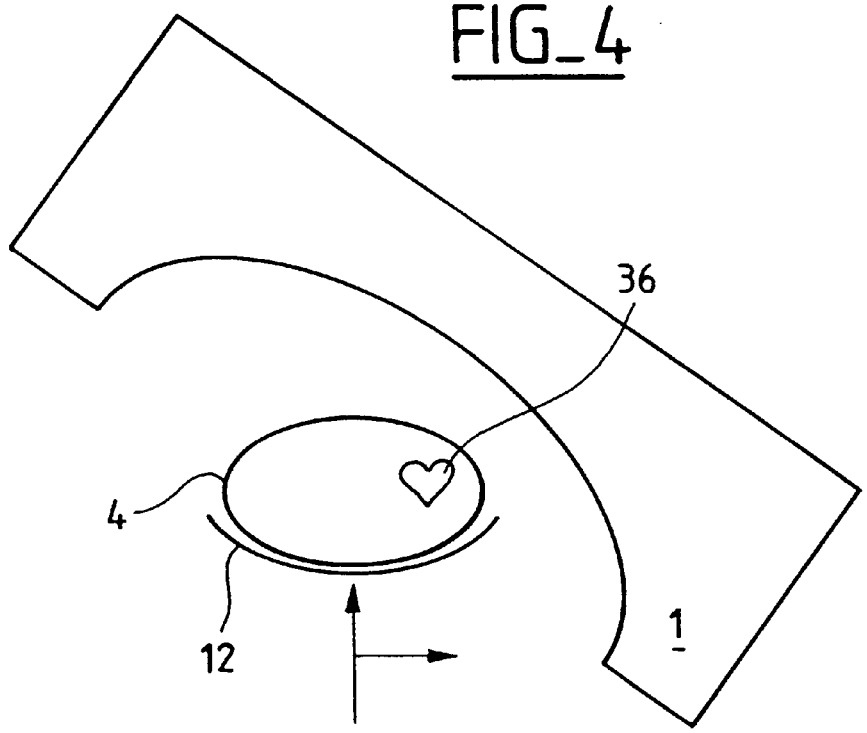

NUCLEAR MEDICINE MACHINE

BACKGROUND OF THE INVENTION

1. Field of the Invention

An object of the present invention is a nuclear medicine machine that can be used to acquire static type measurement data, where the machine is fixed with respect to the patient being examined, as well as dynamic type data where it is mobile with respect to the patient. Operations of dynamic acquisition are essentially used to take tomography shots. In acquisition operations of this kind, the motion of the machine is most often a rotation of its detectors around the patient.

The detectors used have a plane input face located above a collimator, with holes that are divergent or parallel, straight or oblique. The collimator is itself placed above a scintillator. This assembly is superimposed on an array of photomultiplier tubes. The photomultiplier tubes are furthermore electronically connected to circuits for the detection and computation of an image. The image results from the totalizing of an operation for counting the number of strokes that occur at a position of the scintillator under the effect of the gamma photons that are emitted by the patient's body and go through the collimator before getting converted into light photons in the scintillator.

The invention is aimed at simplifying the making of such machines so as to reduce the cost of manufacture.

2. Description of the Prior Art

To take tomographic shots, there is a known way of shifting the detectors of a nuclear medicine machine around the patient's body so as to acquire a certain number of views along angles of incidence extending over a range of at least 180°. To accelerate the acquisition of the information elements needed to prepare an image in tomography, ways have already been worked out for building machines with two or even three detectors capable, of approaching the patient in order to accommodate different sizes of patients as well as the difference in the way in which a patient is presented depending on whether he is seen from the side, the front or the back. The machines are furthermore provided with a stand that bears the detectors and is capable of making them rotate around the patient's body so as to acquire views at all the necessary angles of incidence. The stand is not static; it rotates.

These machines of a known type have the drawback of requiring a complex kinematic arrangement resulting in a high cost of manufacture. For, since their weight is great, the detectors can be handled only if they are counter-balanced by dead weights of comparable weight, which also have to be put into motion.

SUMMARY OF THE INVENTION

The aim of the invention, therefore, is to simplify the mechanical configuration of the stand of a nuclear medicine machine and the operation for putting the stand into motion. In the invention, quite simply, the detector will be held fixed, even during the acquisition of the tomographic shots. In this case, its extra cost of manufacture is very greatly reduced. However, to resolve the problems related to the diversity of the angles of incidence needed to constitute the tomographic shots, the input surface of the detector will be curved. It will have a concave shape so as to be able to contain, at least partly, the body of the patient being examined in the cavity formed. With the detector then encompassing the patient's body, preferably on a range of 180°, all the necessary angles of incidence are acquired without the detector having to be made to rotate around the patient's body to acquire several successive views.

An object of the invention therefore is a nuclear medicine machine comprising a detector provided with an input surface to receive gamma rays emitted by the body of a patient positioned so as to be before this input face, and means for the detection and computation of an image resulting from this reception, wherein the input surface of the detector has the shape of a concave curve.

BRIEF DESCRIPTION OF THE DRAWINGS

The invention will be understood more clearly from the following description, and from the appended figures. These figures are given purely by way of an indication and in no way restrict the scope of the invention. Of these figures:

FIG. 1 gives a schematic view in perspective of a machine according to the invention;

FIG. 2 shows a schematic view of elementary motions entailing a simple kinematic arrangement, to which the detecters of the machine of the invention may be subjected;

FIG. 3 shows the appearance, in a front view, of a machine according to the invention with its protection hood;

FIG. 4 shows a preferred use of the machine of the invention.

MORE DETAILED DESCRIPTION

FIG. 1 shows a nuclear medicine machine according to the invention. It has a detector 1 provided with an input face 2. This input face 2 is the face by which there penetrate gamma rays 3 emitted by the body of a patient 4. The patient 4 is positioned so as to be before the face 2. The detector has detection means of a standard type. These detection means are essentially, in one example, a collimator 5, a scintillator 6 and a set 7 of photomultipliers such as 8. However, any other system of detection can also be envisaged. In particular, it is possible for the detector to possess no collimator, and to be a PET type detector, efficient detection being ascertained by a simultaneous detection on two facing detectors. Similarly, the tubes 8 may be replaced by solid semiconductor detectors.

Under the effect of a gamma photon 3 which goes through the collimator 5, the scintillator 6 sends out a light photon 9 whose energy excites the dynodes of the photomultiplier tubes 8 of the set 7. The photomultipliers 8 then deliver an output signal at their anode. These output signals are collected and processed by a processing circuit 10. The circuit 10 enables the localizing of the place 11 at which the gamma emission 3 has occurred in the body.

According to a major characteristic of the invention, the input face 2 of the detector 1 has the shape of a concave curve. In a preferred example, the curvature of the face 2 is that of a cylinder whose directrix is elliptical, in fact semi-elliptical, intersected along a plane passing through the major axis of the ellipse. The generatrix lines are horizontal. In one example, the length of the major axis of the ellipse is of the order of 50 cm. It would appear that eccentricity of this kind is well suited to the shape of the body of a stout patient 4 reclining, on his back or stomach, on an examination bed 12.

FIG. 1 also shows a box 13, in which there is placed another detector that is identical to the detector 1 and has an input face 14, also with the shape of a concave curve, preferably symmetrical to the shape of the curve of the face 2, with respect to a horizontal plane 15 passing through the major axis of the ellipse.

Rather than providing for an elliptical shape, it is possible to provide for circular cylindrical shapes or also ovals that have different shapes and could possibly approach the shape of the patients' body more closely.

In certain cases, the making of a detector like the detector 1 or the one contained in the box 13 requires the making of a collimator. In one example, the collimator, to begin with, will be a flat collimator of requisite thickness, made of lead. To obtain this flat collimator, parallel or other holes are drilled. These holes are distributed according to a choice corresponding to the compromise of detection to be chosen. Once these holes have been drilled, the collimator thus drilled is shaped around an oval, elliptical or circular chuck. This shaping is done by compression. This shaping is particularly easy if the material of the collimator is lead. According to another technique, it is possible to place a sheet of the material used to make the collimator, shaping it around the chuck of requisite size, and to make the drilled holes after this shaping operation.

If need be, the distribution of the drilled holes in the collimator will differ as a function of the radius of curvature of the collimator. For example, in regions where the radius of curvature is small, the regions 16 and 17 in FIG. 1, the number of holes could be higher, and the size of the holes could be smaller than, respectively, the number and size of the holes located in the part 18 where the radius of curvature is greater. If the shape is circular, then preferably the distribution of the holes will be uniform.

The scintillator 6 against which the collimator 5 is placed will preferably be a scintillator obtained by milling. In a polycrystalline block of sodium iodide or cesium iodide (which is softer) the unwanted parts that correspond to the cavity and go beyond the requisite thickness will be cut out by gradual removal. It is possible, in this way, to manufacture scintillators measuring 0.95 cm (⅜ inch), 1.27 cm (½ inch), 1.90 cm (¾ inch), and 2.54 cm (1 inch) which, the greater the thickness of the crystal, provide for a gain in sensitivity at the high energy values. This, for example, is especially valuable if fluoride 18 (fluorodesoxyglucose) emitting at 511 KeV is used as an emission agent in being injected into a patient's body. Measured along the axis 19 of the patient, the collimator 5, the scintillator 6, and of course the photomultiplier array 7 have a length that depends on the expected use of the machine. The axis 19 is parallel to the length of the patient. For example, if the machine is used up to 60% to perform whole-body type examinations, up to 30% to perform cardiac type examinations, and up to 10% to perform renal type examinations, then, depending on the resources available to the party acquiring the machine, a choice will be made to have a big machine with a big length (for example one meter) or a smaller machine which is shorter. The length of the crystal will in fact determine the efficiency of the machine. On the contrary, if the 90% of the examinations are cardiac type examinations, then a small machine could suffice.

As a variant, the scintillator 6 will be forged. In this case, preferably a cesium iodide crystal will be used. The forging will be done as in the case of the first embodiment referred to for the collimator. In yet another variant, the collimator will be constituted by a set of several crystal elements to be attached to one another.

If the photomultiplier tubes 8 are placed in this assembly, it will be done, as in the prior art, by using a structure borne by the box 13. Preferably, the tubes will be attached by their input face against the scintillator 6. In the example, 24 photomultiplier tubes with input faces 8 cm×8 cm square are positioned along the sectional profile of the detector. Twelve of these tubes are also positioned on a length of one meter. The detector then has 288 photomultiplier tubes.

FIG. 2 gives a view, in a variant with two detectors, of a preferred use of the invention. When the patient 4 is small, he is made to recline on a couch 12 suited to his size. Then, rather than keeping the detectors, as in FIG. 1 in a position where they face each other, they will be shifted laterally relative to the cavity to vary the lateral cross-sectional area of the cavity. The detector 1 placed on top is shifted horizontally leftwards, while the detector 13 placed below shifts horizontally rightwards. As needed, only one of the two detectors is shifted. The bed is inserted into the resultant cavity. Thus, the cavity formed in the common space between the two concave curves of the input faces of the detectors is reduced. In this way, the sensitivity is improved and the detectors are positioned as closely as possible to the body of the patient 4.

Since, in this case, the elliptical shape is no longer as well suited to the small size of the patient (for example that of a child) it is furthermore provided, preferably, that the detectors will be made to pivot with respect to horizontal axes extending longitudinally relative to the cavity. The detector 1 may for example pivot about a horizontal axis 20, parallel to the axis 19. The detector 1 is then borne, firstly, by a shaft passing through the axis 20 and, secondly, by a suspension 21. It may also be borne by the shaft 20 alone. The suspension 21 comprises, in a schematic example shown, a hook 22 that catches the detector 1, a pulley 23 that holds the hook 22, a carriage 24 travelling on the ceiling portion of a stand 25 (see FIG. 3) of the machine and a pulley 26 supported by the carriage 24. A cable 27 fixed to pulley 26 and rotating about the pulley 23 and the pulley 26 gets wound on a shaft that is driven by a motor 28. Depending on the action of the motor, the detector 1 takes a tilt tending to make the input face 2 approach or move away from the patient's body. The motor 28 is, for example, controlled by a set of buttons at the disposal of an operator who acts in such a way that the machine is placed as closely as possible to the body of the patient 4.

If need be, the axis 20, rather than being placed at the position of the oval with the greatest curvature, could be placed at the tip of the oval in the region 18. The advantage of the second approach is that the shaft 29 thus placed corresponds to a state of equilibrium of the detector on its suspension. In this case; rather than providing for a translation of the axis 20, it is necessary to provide for a vertical and horizontal translation of the axis 29 so that the detector, in combination with a rotation 30, is made to come closer to the patient's body.

For the box 13, an axis 31 is the counterpart of the axis 20 while a jack system 32 supported on the ground by a carriage 33 fulfils a role similar to the suspension 21. In the position shown in the figure, the volume of the resultant cavity is reduced and the detection is more efficient.

At the time of the acquisition of the measurement data elements necessary for the preparation of a tomography image, it is not necessary to make the machine of the invention rotate since information coming from all directions is acquired without motion. It is then possible to make profitable use of acquisition times that were devoted to each of the views in the prior art and acquire, with the invention, a single view with a greater dynamic range, while remaining for a longer time in the single measuring position.

FIG. 3 gives a view, in the stand 25, of the apertures 34 and 35 made in a front face of this stand that enable the sliding of the shafts corresponding to the axes 20 and 31 respectively. The apertures 34 and 35 are not made at the same height. The aperture 34 is located in a higher position.

FIG. 4 gives a view, in an exemplary use of the machine of the invention with a single detector, of a preferred position used to acquire all the information needed to constitute a tomographic image of the heart 36 of the patient 4. In this example, while the layer 12 has been lifted and shifted rightwards to approach the patient's heart as closely as possible to the inner face of the cavity, the detector 1 has been tilted so that the major axis of the ellipse is tilted by 45° to the horizontal.

For the calibration of the machine, it is possible to make a mathematical model of the effects of the distribution of the detection surfaces of the photomultiplier tubes on the curved surface of the detector. It is possible, preferably, to place phantoms instead of the body 4 and acquire the corresponding images and then make the corrections of the acquisition system so that the images obtained are as close as possible to the theoretical images.

For reasons of manufacture, it may be difficult to make sharp curves in the alignment of the major axis of the oval (zones 16,17). It is then possible to accept a compromise with half-shells that are not perfectly elliptical but possess, for example, an end slope 37 (FIG. 2) that is not strictly perpendicular 38 to the direction 39 of the major axis of the oval. The corrections made by the passage of the phantom make it possible here again to overcome the distortions of detection that result from this feature.

With the static solutions of FIG. 1 or, after shifting, the solutions of FIG. 2, it is possible to make a very low-priced machine. It is no longer necessary to make the counter-weights and the corresponding mechanical devices known in the prior art. Furthermore, at the time of the acquisition, since nothing moves, there is a greater precision of the computation for the reconstruction of the images.

Finally, in the case of a use of the type shown in FIG. 2, it is also possible to make collimators whose holes are oriented towards the useful section (and not towards the regions where the patient's body is not located) so as to compensate in advance for a deficit of detection that would result from a radial detector.

We claim:

1. A nuclear medicine machine comprising: two distinct detectors, each of which is provided with a concave curved input surface configured to receive gamma rays emitted by the body of a patient reclining in a cavity formed between said input surfaces, and means for detecting and computing an image resulting from the reception of gamma rays on said input surfaces of said detectors from the body of the patient, said detectors being movable relative to one another so as to alter a lateral cross-sectional area of said cavity.

2. A machine according to claim 1, wherein each detector is horizontally translatable relative to said cavity.

3. A machine according to claim 1, wherein each detector is pivotable about an associated horizontal pivot axis extending longitudinally of said cavity.

4. A machine according to claim 1, wherein the concave curved shape of the input surface of each of said detectors is that of a cylinder whose directrix has a semi-oval shape.

5. A machine according to claim 4, wherein a major axis of the semi-oval has a length of 1 m and a minor axis has a length of 0.5 m.

6. A machine according to claim 4, wherein the directix of said cylinder is semi-elliptical.

7. A use of a machine according to claim 1 wherein, before acquiring measurement data elements, at least one of said detectors is tiltable with respect to the horizontal, said tilting occurring about a pivot axis extending longitudinally of said cavity.

8. A nuclear medicine machine comprising:
   (A) two distinct detectors which face one another to form a patient-receiving cavity therebetween, wherein said cavity extends longitudinally in the direction of a patient lying therein, wherein each of said detectors has a concave curved input surface which faces said cavity and which is positioned to receive gamma rays emitted by the body of the patient, and wherein at least one of said detectors is movable relative to the other of said detectors so as to vary a lateral cross-sectional area of said cavity; and
   (B) means for detecting and computing an image resulting from the reception of gamma rays on said input surfaces of said detectors.

9. A machine according to claim 8, wherein at least one of said detectors is pivotable about a horizontal pivot axis extending longitudinally relative to said cavity.

10. A machine according to claim 8, wherein at least one of said detectors is movable horizontally laterally relative to said cavity.

11. A machine according to claim 8, wherein both of said detectors are movable relative to said cavity.

12. A machine according to claim 11, wherein each of said detectors (1) is pivotable about a corresponding pivot axis, each of said pivot axes extending longitudinally relative to said cavity, and (2) is additionally translatable horizontally laterally relative to said cavity.

13. A method comprising:
   (A) providing two distinct detectors which face one another to form a patient-receiving cavity therebetween, wherein said cavity extends longitudinally in the direction of a patient lying in said cavity, and wherein each of said detectors has a concave curved input surface which faces said cavity;
   (B) varying a lateral cross-sectional area of said cavity by moving at least one of said detectors relative to the other of said detectors;
   (C) emitting gamma rays from the patient within said cavity and impinging said gamma rays on said concave curved input surfaces of said detectors; and
   (D) detecting and computing an image resulting from the reception of said gamma rays on said input surfaces of said detectors.

14. A method according to claim 13, wherein the varying step comprises pivoting at least one of said detectors about a horizontal pivot axis extending longitudinally relative to said cavity.

15. A method according to claim 13, wherein the varying step comprises moving at least one of said detectors horizontally laterally relative to said cavity.

16. A method according to claim 13, wherein the varying step comprises moving both of said detectors relative to said cavity.

17. A method according to claim 16, wherein the varying step comprises (1) pivoting both of said detectors about a corresponding pivot axis, each of said pivot axes extending longitudinally relative to said cavity, and (2) translating both of said detectors horizontally laterally relative to said cavity.

* * * * *